United States Patent [19]

Shackelford

[11] 4,243,071
[45] Jan. 6, 1981

[54] SAMPLE INJECTION VALVE

[75] Inventor: Carl L. Shackelford, San Pablo, Calif.

[73] Assignee: Altex Scientific, Inc., Berkeley, Calif.

[21] Appl. No.: 936,174

[22] Filed: Aug. 23, 1978

[51] Int. Cl.³ .................................. F16K 11/02
[52] U.S. Cl. .................... 137/625.46; 73/422 GC
[58] Field of Search ............ 137/625.46, 625.19, 137/625.47, 625.43; 73/422 GC, 422 TC

[56] References Cited

U.S. PATENT DOCUMENTS

| 3,045,702 | 7/1962 | Nakata | 73/422 GC |
| 3,071,005 | 1/1963 | Skidmore | 73/422 GC |
| 3,368,385 | 2/1968 | Harvey, Jr. | 73/422 GC |
| 3,411,525 | 11/1968 | Auger | 137/625.46 X |
| 3,747,630 | 7/1973 | Hurrell | 137/625.46 X |
| 3,868,970 | 3/1975 | Ayers et al. | 137/625.46 |
| 4,059,009 | 11/1977 | Ball | 73/422 GC X |
| 4,068,528 | 1/1978 | Gundelfinger | 73/422 GC |

FOREIGN PATENT DOCUMENTS

| 800212 | 8/1958 | United Kingdom . |
| 855234 | 11/1960 | United Kingdom . |
| 996229 | 6/1965 | United Kingdom . |
| 1487468 | 9/1977 | United Kingdom . |
| 1495662 | 12/1977 | United Kingdom . |

Primary Examiner—William R. Cline
Attorney, Agent, or Firm—Bielen and Peterson

[57] ABSTRACT

A sample injection valve using a member having four ports as a fluid system inlet, a sample injection inlet, a fluid system outlet, and a vent. The valve also uses a fluid sample reservoir and includes a controller for simultaneously connecting the fluid system inlet and outlet and interposing the fluid reservoir between the sample injection inlet and the vent. A switch changes the position of the fluid reservoir to one of interposition between the fluid system inlet and the fluid system outlet.

11 Claims, 6 Drawing Figures

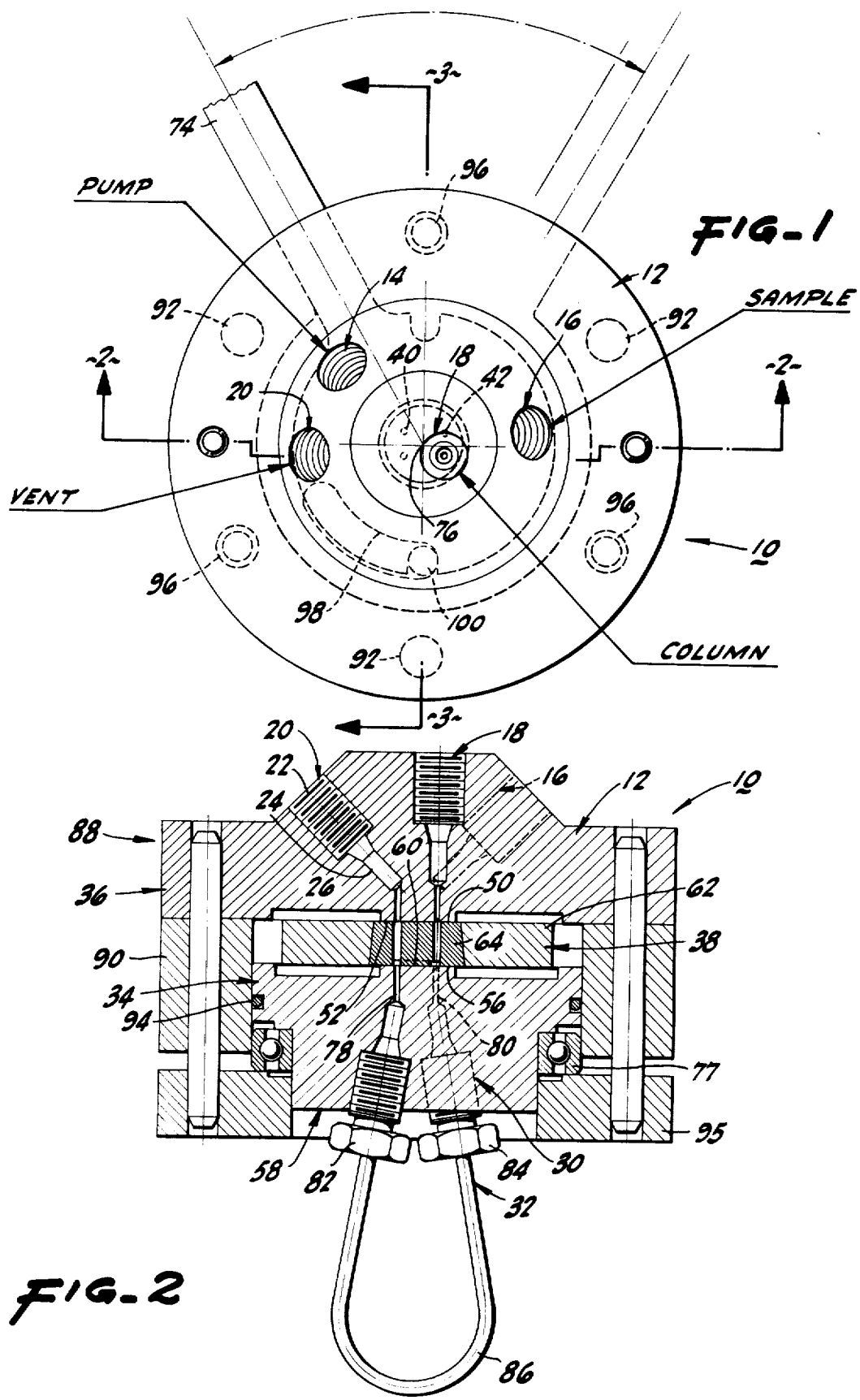

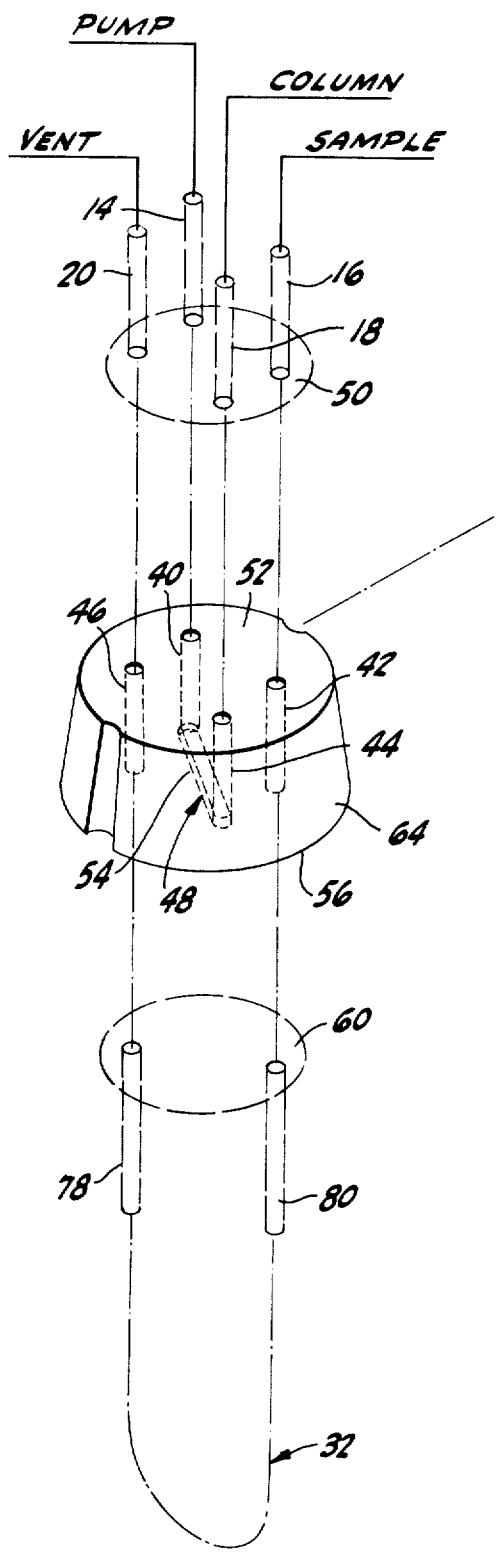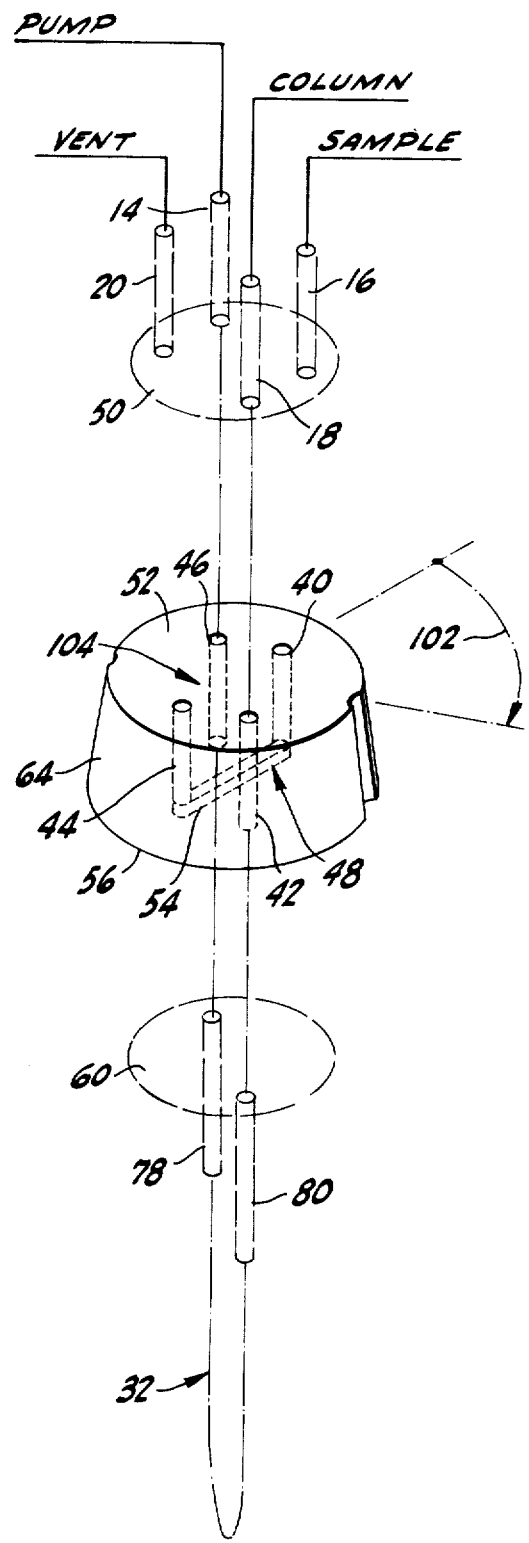

SAMPLE INJECTION VALVE

BACKGROUND OF THE INVENTION

The present invention relates to a novel sample injection valve.

Separations of fluids are inherent in the liquid chromatographic process. Modern fluid or liquid chromatographic systems operate under very high pressures ie: up to 10,000 psi. Sample injection for the purpose of analysis and testing requires valving arrangements to permit loading and injection of the sample, as well as flushing of the sample reservoir.

Past systems of sample injection have involved the use of six port valves in conjunction with syringe injectors. The six port valve of the prior art usually included a stator and rotor acting in concert to connect or align ports thereon.

Existing six port valves encounter clogging problems due to the presence of particulate matter generated by the relative movement of the rotor and stator. It is known that the edges of the ports tend to scrape or spall valve facing materials and thus create particulate matter which aids in the clogging process hereinbefore described. Also, the mated plastic surfaces of the stator and rotor tend to deform under the extremely high fluid pressures encountered. Such deformation can lead to leakage and/or misdirection of carrier fluids. In addition, many prior valve designs suffer from having dead volume spaces which result in the obtaining of inaccurate results during the down stream analysis of the fluids.

SUMMARY OF THE INVENTION

In accordance with the present invention a novel and useful injection valve is provided which overcomes many of the problems encountered in the prior art.

The valve of the present invention includes a first member having four ports. The first port serves as a fluid system inlet, the second port serves as the sample injection inlet, the third port serves as the fluid system outlet, and the fourth port serves as a vent. The valve also includes means for retaining a fluid sample which may be in the form of a loop or tube having a preselected volumetric capacity.

Control means is further provided for simultaneously connecting the first and third ports of the first member and the fluid retaining means to the second and fourth ports of the first member. In other words, the control means connects the fluid system inlet to the fluid system outlet and interposes the fluid retaining means between the second and fourth ports. This aspect of the invention permits the loading of a sample in the fluid retaining means while the pressurized fluid system is isolated therefrom. The control means may further embrace a second member having first, second, third, and fourth ports, each port being capable of corresponding interconnection with the first, second, third, and fourth ports of the first member. Again the fluid sample retaining means would be connected between the second and fourth ports of the second member. The invention further has shunt means for connecting the first and third ports of the second member at a point spaced from the interconnection of the interconnection of the first and third ports between the first and second members. Such shunt means may take the form of providing the second member with a first surface adjacent the first member and a second surface in sealing engagement with a third member. The second surface of the second member would include a groove formed between the first and third ports. The sealing engagement between the second surface of the second member and the third member forms a fluid channel between the first and second ports of the second member. Thus, the fluid flows from the first port of the first member to the first port of the second member found on the first surface of the second member, to the shunt means. At this point the fluid travels through the channel formed between the second surface of the second member and a third member to the third port on the second surface of the second member. Finally the fluid completes its journey by traveling through the third port to the second surface of the second member and from there to the third port of the first member.

As another element of the invention has means for changing the position of the fluid retaining means from connection between the second and fourth ports of the first member to connection between the first and third ports of the first member. This may be accomplished by also including means for moving the second member relative to the first member. Such member moving means changes the interconnection of the second and fourth ports of the second member from interconnection with the second and fourth ports of the first member to interconnection with the first and third ports of the first member. Thus, the fluid retaining means positions in the fluid stream between the fluid system inlet and the fluid system outlet. In the case of a liquid chromatography system the fluid retaining means or loop, is placed between a high pressure metering pump and a liquid chromatography column.

The invention as described hereinbefore may be deemed to include a rotor composed of the second and third members movable with respect to the first member which may be deemed a stator. A housing may be provided to support the rotor and stator in adjacent disposition. The relative movement between the stator and rotor may be easily accomplished by providing handle means affixed to the second member and extending to the exterior of the housing. In such case the third member would be affixed to the second member for concomitant movement therewith. The fluid retaining means may take the form of a loop affixed to the exterior of the third member in spaced disposition from the heretofore described second surface of the second member.

The relative movement between the first and second members or the rotor and stator may be pivotal. In which case, pivot means is provided, including a bearing, which will permit accomplishment of the same.

The relative movement between the first member and the second member may be facilitated by providing said second member with a relatively hard first portion surrounding a relatively soft second portion. A second portion would have self lubricating characteristics and contain the first, second, third, and fourth ports thereof. The ports of the second member may be constructed to be of uniform cross-sectional dimensions to eliminate any dead volumes therewithin. In addition, the invention may further comprise means for blocking the second port of the first member simultaneously with the activation of the position changing means. Thus, the sample injection port is isolated from the vent port of the first member. This provision is extremely useful with an auto-sampler which requires the maintaining of pressure therein between injection of various samples to the fluid system.

It may be apparent that a new and useful sample injection valve has been described.

It is therefore an object of the present invention to provide a sample injection valve for a pressurized fluid system which employs only four ports employing movable portions.

It is another object of the present invention to provide a sample injection valve useful in a pressurized fluid system which reduces wear between the stator and rotor and concurrently reduces the possibility of clogging of the ports.

It is another object of the present invention to provide a sample injection valve useful in pressurized fluid systems which is simpler in construction than the prior art valves and is less expensive to construct.

Yet another object of the present invention is to provide a sample injection valve useful in pressurized fluid systems which has a variety of sample reservoirs which are easily accessible and interchangeable with each other.

Still another object of the present invention is to provide a sample injection valve useful in pressurized fluid systems which is reliable under typical high pressure liquid chromatography conditions, including compatibility with auto samplers.

The invention possesses other objects and advantages especially as concerns particular features and characteristics thereof, which will become apparent as the specification continues.

BRIEF DESCRIPTION OF THE DRAWINGS

FIG. 1 is a top plan view of the valve with a slightly broken portion.

FIG. 2 is a view taken along line 2—2 of FIG. 1.

FIG. 5 is an exploded schematic view representing the load position of the valve.

FIG. 6 is an exploded schematic view representing the valve of the sample injection position.

Figure 4:
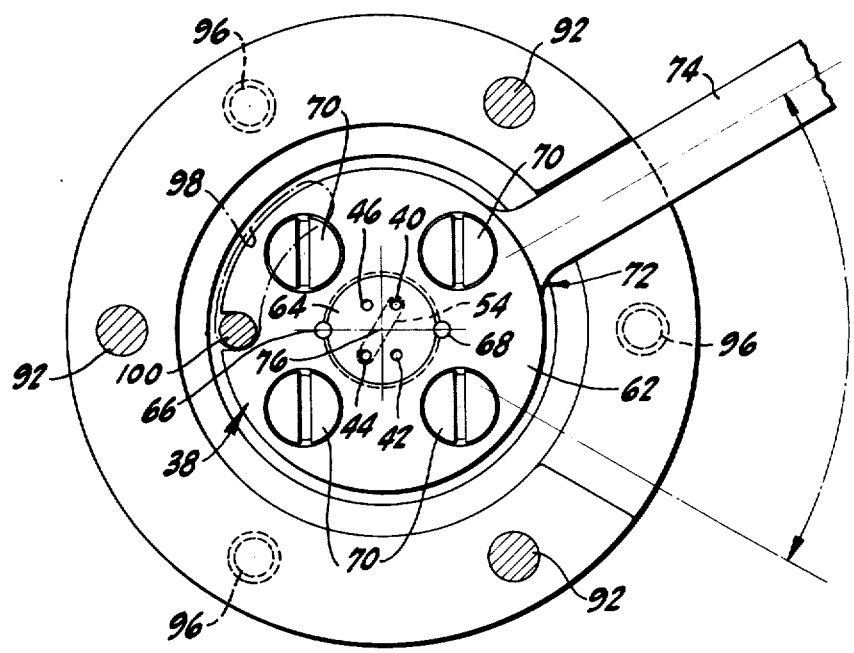
FIG. 4 is a view taken along line 4—4 of FIG. 3.

Various aspects of the present invention will evolve from the following detailed description of the preferred embodiments thereof which should be taken in conjunction with the accompanying drawings.

For a better understanding of the invention, references made to the following detailed description.

DESCRIPTION OF THE PREFERRED EMBODIMENTS

The invention as a whole is represented in the drawings by reference character 10 and includes as one of its elements a first member 12. As illustrated on FIG. 1, first member 12 includes first port 14 which serves as a fluid system inlet. In the case of a liquid chromatography system port 14 would serve as a conduit for the output of a high pressure metering pump, not shown. Second port 16 of first member 12 is the sample injection inlet. Likewise, third port 18 of first member 12 acts as the fluid system outlet which normally feeds into a packed column when employed in a liquid chromatography system. Fourth port 20 of first member 12 functions as a vent to the external atmosphere. Each port of first member 12 is similar in construction. Using fourth port 20 of first member 12 as an example, FIG. 2, it is apparent that one end portion of each port includes an internally threaded fitting 22 which tapers into a funnel shaped intermediate portion 24 and terminates into an end portion 26, an opening of substantially uniform diameter. Opening 26 may be circular in cross-sectional configuration and have a diameter of approximately a quarter of a millimeter in many high pressure systems. It should be apparent that each input to each threaded portion of the ports of first member 12 would include corresponding externally threaded fittings for engagement thereof, not shown.

The valve 10 further includes, as one of its elements, control means 30 which simultaneously connects first port 14 to third port 18 of member 12. Control means 30 also connects fluid retaining means 32 to second port 16 and fourth port 20 of member 12. Fluid retaining means 30 will be more fully described as the specification continues.

Figure 3:
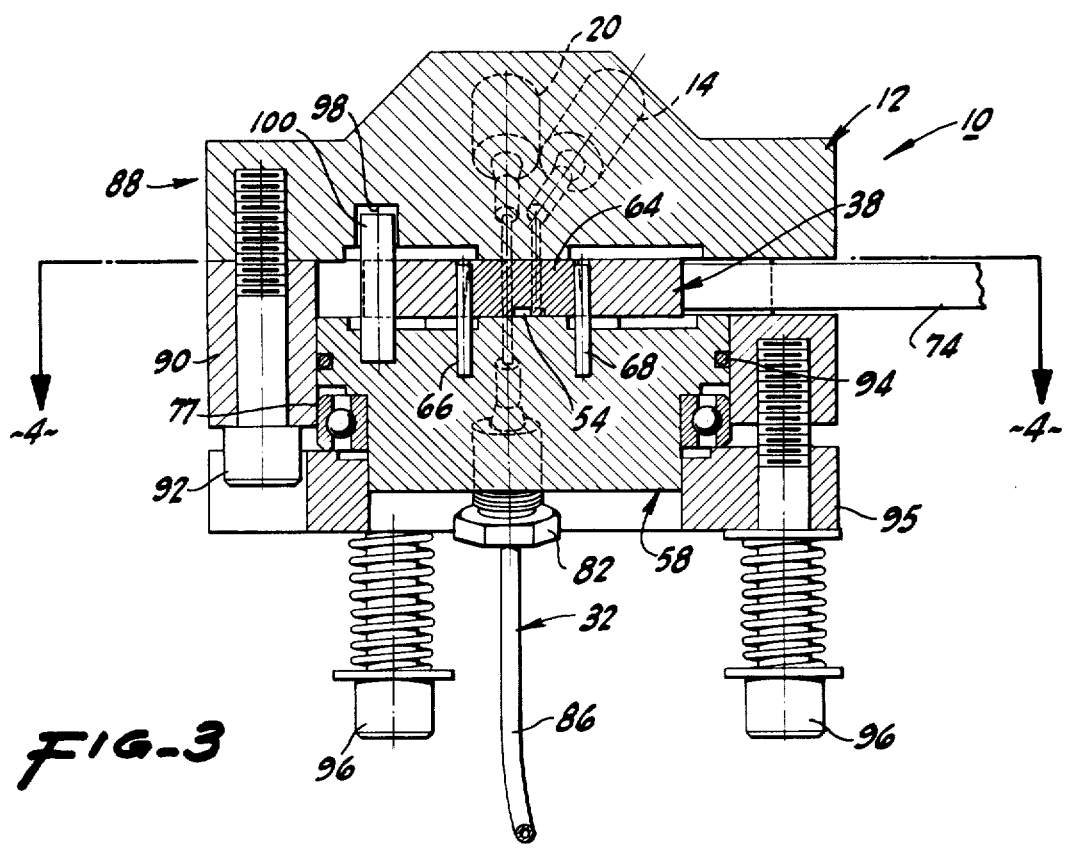
FIG. 3 is a view taken along line 3—3 of FIG. 1.

Control means 30 may take the form of a rotor 34 which is movable in relation to a stator 36 which is essentially member 12. Rotor 34, FIGS. 2, 3, and 4, may embrace a second member 38 having first port 40, second port 42, third port 44, and fourth ports 46, which are capable of corresponding interconnection with ports 14, 16, 18, and 20 of first member 12, FIG. 1. As shown in FIGS. 1, 2, and 3, first port 14 of member 12 connects to first port 40 of second member 38. Similarly, ports 16 and 42, 18 and 44, and 20 and 46, also interconnect. Such interconnection of the various ports is intended to mean fluid interconnection such that the fluids may freely pass from one port to the corresponding aligned port. Second member also includes shunt means 48 which is located a selected distance from the interface between first member 12 and second member 38 at surfaces 50 and 52 thereof. Shunt means 48 may externalize in a groove 54 on surface 56 of second member 38. A third member 58, FIGS. 2 and 3, has a surface 60 which sealingly engages surface 56 of second member 38. Thus groove 54 becomes a fluid channel between first port 40 and third port 44 of second member 38, FIG. 4.

Second member 38 may be constructed in the form of a relatively hard first portion 62 which may be constructed of metals such as, but not limited to stainless steel, and a relatively soft second portion 64 which contains ports 40, 42, 44, and 46. First portion 62 surroundingly engages second portion 64 which is held rigidly in place by pins 66 and 68 emanating from third member 58, FIGS. 3 and 4. It should be noted that second member 38 and third member 58 are rigidly fixed to one another. Inner portion 64 of second member 38 may be constructed of Teflon, Kel-f or other materials possessing self lubricating characteristics. Thus, surface 52 of second member 38 may be formed as part of inner portion 64 and therefore, exhibit lubricating properties against relatively hard surface 50 of member 12. Fastening means 70 securely holds second member 38 to third member 58.

The valve 10 also has as one of its elements means 72 for changing the position of fluid retaining means 32 from connection between ports 16 and 20 of first member 12 to connection between ports 14 and 18 of the same. Such means may take the form of handle means 74 for moving second member 38 in relation to first member 12. Such movement would change the position of ports 42 and 46 of second member 38 from interconnection with ports 16 and 20 of first member 12 to interconnection with ports 14 and 18 of first member 12. The embodiment illustrated in the drawings depicts this movement as being rotary about pivot 76. Bearing 77 aids the rotary motion of second member 38 in relation to first member 12.

Fluid sample retaining means 32 may take the form of third member 58 having a first port 78 and a second port 80 being similar in construction to fourth port 20 of first member 12, hereinbefore described. As shown in FIG. 2, a fluid sample retaining means 32 includes threaded fittings 82 and 84 located on the terminals of a reservoir 86. Reservoir 86 may take the form of a tubular loop which may be selectively sized to hold a desired volume of fluid sample. Fluid sample retaining means 32 possesses the characteristic of having easily interchangeable reservoirs 86. As shown in the drawings, port 78 and 80 of third member 58 interconnect with ports 42 and 46 of FIG. 4.

A housing 88 supports rotor 34 and stator 36 in adjacent disposition. Housing 88 is formed from a body 90 which mounts to a portion of first member 12 by fastening means 92. Third member 58 includes O-ring 94 for sealing engagement to body 90. Clamp 94 including fastening means 96 encloses the bottom portion of third member 58. Dowell pin 100 moves in a restricted manner within slot 98, thus defining the movement of rotor 34.

In operation, FIGS. 5 and 6, the user connects the fluid inlet and outlet to ports 14 and 18 of first member 12, also, a sample injection device, not shown, is connected to port 16 of first member 12. Rotor 34 consisting of second and third members, 38 and 58, is aligned such that ports 40, 42, 44, and 46 of second member 38 correspondingly interconnect and align with ports 14, 16, 18, and 20 of stator 36. At this point it may be seen that the fluid inlet or pump enters port 14, travels through port 40, shunt 48, and port 44 to the fluid outlet or column port 18 of first member 12. The pressurized fluid system is free to flow in this mode. At the same time, a sample may be injected through port 16, into port 42 to fluid sample retaining means 32. Unwanted fluids or gasses are forced through port 78, 46, and 20 to the external atmosphere. Turning to FIG. 6 we see that rotation of rotor 34 in the direction of arrow 102 has caused realignment and therefore reconnection of the ports. A fluid inlet port 14 now causes the fluid sample within the fluid sample retaining means to flow to the fluid outlet or column via ports 14, 44, 78, 80, 42, and 18. It may be seen also that such rotation brings into play means 104 for blocking port 16 of stator 36 or first member 12. In other words, ports 40 and 44 interconnected to shunt means 48 are isolated by face 50 of first member 12. Means 104 may be used to control the action of auto samplers which can be connected to port 16.

While in the foregoing specification embodiments of the invention have been set forth in considerable detail for the purposes of making a complete disclosure of the invention, it will be apparent to those of ordinary skill in the art that numerous changes may be made in such details without departing from the spirit and principals of the invention.

What is claimed is:

1. A sample injection valve especially useful for injecting a fluid sample into a pressurized fluid system comprising:
   a. a first member having a first port as the fluid system inlet, a second port as the sample injection inlet, a third port as the fluid system outlet, and a fourth port as a vent;
   b. means for retaining a selected amount of fluid sample;
   c. control means for simultaneously connecting said first port of said first member to said third port of said first member, and connecting said fluid sample retaining means to said second port and said fourth port of said first member; said control means comprising:
      a second member having first, second, third, and fourth ports, said fluid sample retaining means being connected to said second member between said second and fourth ports thereof for communication therewith, said second member further including shunt means for connecting said first and third ports of said second member; said second member being mounted for communication of said first, second, third, and fourth ports thereof with said first, second, third, and fourth ports of said first member; and
   d. means for moving said second member in relation to said first member to change the position of said fluid sample retaining means from connection between said second and fourth ports of said first member to connection between said first and third ports of said first member.

2. The sample injection valve of claim 1 in which said connection of said fluid sample retaining means to said second member between said second and fourth ports thereof, and said shunt means for connecting said first and third ports of said second member, are spaced from said communication of said first and third ports of said first, second, third and fourth ports of said first and second members.

3. The sample injection valve of claim 2 in which said shunt means comprises said second member having a first surface adjacent said first member and a second surface in sealing engagement with a third member, said second surface of said second member includes a groove between said first and third ports of said second member, said sealing engagement between said third member and said second surface of said second member and said groove on said second surface of said second member forming a fluid channel between said first and third ports of said second member.

4. The sample injection valve of claim 3 in which said fluid sample retaining means comprises said third member having a first and second port interconnected to said second and fourth ports of said second member, said first and second ports of said third member being connected to a reservoir spaced from said interconnection of said first and second ports of said third member to said second and fourth ports of said second member.

5. The sample injection valve of claim 4 in which said second and third members comprise a rotor movable with respect to said first member which comprises a stator, said rotor and stator including a housing for supporting said rotor and stator in adjacent disposition.

6. The sample injection valve of claim 5 in which said means for moving said second member relative to said first member further comprises handle means fixed to said second member and extending to the exterior of said housing.

7. The sample injection valve of claim 6 in which said means for moving said second member relative to said first member further includes pivot means for rotating said second member relative to said first member.

8. The sample injection valve of claim 7 in which said pivot means further includes a bearing.

9. The sample injection valve of claim 1 in which said second member includes a relatively hard first portion surrounding and engaging a relatively soft second portion having self-lubricating characteristics, said first, second, third, and fourth ports of said second member being located in said second position thereof.

10. The sample injection valve of claim 9 in which said first, second, third, and fourth ports of said second member are uniform openings therethrough.

11. The sample injection valve of claim 1 in which said means for moving said second member in relation to said first member additionally includes means for blocking communication of said second and fourth ports of said first member with said second and fourth ports of said second member simultaneously with said changing of said position of said fluid sample retaining means from connection between said second and fourth ports of said first member to connection between said first and third ports of said first member.

* * * * *